United States Patent [19]

Pellegrino

[11] Patent Number: 4,822,569
[45] Date of Patent: Apr. 18, 1989

[54] ROTARY SHEAR VALVE WITH CLEANING FEATURE AND METHOD OF USING SAME

[75] Inventor: Ernest N. Pellegrino, Bridgeport, Conn.

[73] Assignee: Fisher Scientific Company, Pittsburgh, Pa.

[21] Appl. No.: 872,336

[22] Filed: Jun. 9, 1986

[51] Int. Cl.⁴ .................. G01N 1/00; B67D 5/00
[52] U.S. Cl. .................. 422/103; 73/863.73; 73/864.12; 251/355
[58] Field of Search .......... 422/103; 73/863.73, 73/864.12; 251/355

[56] References Cited

U.S. PATENT DOCUMENTS 4,587,219  5/1986  Claren et al. .............. 422/103 X
4,702,889  10/1987  Cabrera et al. .............. 422/103
4,726,932  2/1988  Feier et al. .............. 422/103

Primary Examiner—Barry S. Richman
Assistant Examiner—Jill Johnston
Attorney, Agent, or Firm—A. Doernberg

[57] ABSTRACT

A rotary shear valve comprising two stators and a rotor is filled with specimen in a first rotary position. Movement of the rotor to a second rotary position divides the specimen into aliquots, one or more of which are dispensed in the second rotary position. A cleaning cycle is provided in which cleaning solution is introduced, with the rotor in a third rotary position, into circumferentially-extending arced grooves formed in the rotor faces, which contacts in the third rotary position those portions of the rotor faces likely to contain smeared specimen. The requirement for disassembly for cleaning is thereby reduced.

9 Claims, 2 Drawing Sheets

ROTARY SHEAR VALVE WITH CLEANING FEATURE AND METHOD OF USING SAME

The present invention relates to rotary shear valves, especially for instruments such as hematology instruments, wherein a specimen (e.g., blood) is introduced in a specimen pathway through the shear valve and at least one aliquot of the specimen is isolated by rotation of the shear valve.

Rotary shear valves are used in a number of different instruments including chromatography instruments (liquid and gas chromatography) and hematology instruments. Using hematology instruments as the prototype, a generally disc-shaped rotor is sandwiched between a front stator and a rear stator. In a first, or home position, a specimen is introduced through a specimen pathway extending normal to the plane of the rotor and of the stators forwardly through the rear stator, a first normal passage of the rotor and through the front stator, through a loop forward of the front stator, back to a passage through the front stator at the same radius but circumferentially spaced (e.g. 105°) and back through the the rotor and the rear stator. Once the specimen has been introduced into this entire pathway, the rotor is rotated (typically 30°) so as to isolate five aliquots of the specimen: two aliquots in two circumferentially spaced passages through the rear stator, two aliquots in two circumferentially spaced passages through the rotor and one large aliquot in a loop pathway which includes two circumferentially spaced passages through the front stator. In the second rotary position, fluid (in the case of hematology instruments generally isotonic diluent) flows through one or more pathways, each of which includes one of the five aliquots of specimen. For example, diluent flowing through an additional passage through the front and rear stator, each aligned with a first passage through the rotor in the second rotary position, can conduct a measured small aliquot of specimen (generally 1.6 microliters) of blood in the first passage through the rotor. In many current hematology instruments, a second pathway includes the large remaining looped portion (which includes two passages through the front stator) so as to conduct the large aliquot (typically 40 microliters) of specimen into a different channel of the instrument. In many hematology instruments, the 1.6 microliter aliquot is admixed with diluent for counting of total cells and other measurements (referred to as the RBC channel) and the diluted large aliquot is admixed with both isotonic diluent and lysing reagent for a series of measurements including total white cells which have survived the lysing process and hemoglobin measurement. Exemplary rotary shear valves are disclosed in U.S. Pat. Nos. 3,567,389 to Coulter et al. (1971), 3,567,390 to Rothermel (1971) and 4,507,977 to Cabrena (1985).

In current rotary shear valves, only those two rotary positions are employed, the first for introducing specimen into the valve, the second for dispensing aliquots of specimen out of the valve. To clear the valve of unused aliquots of specimen, as well as any residue of the aliquots which are used, it is normal to flush the dispensing pathways in the second rotary position and then the specimen pathway in the first rotary position with fluid (in the case of a hematology instrument with isotonic diluent) before introducing the next sample. It should be appreciated, however, that such rinsing may not always remove the last residue of specimen from these pathways and other passages; furthermore, some residue of specimens may form elsewhere in the valve, in particularly along the surfaces by which the rotor contacts one of the stators, especially near the radial position of the passages through the rotor. Accordingly, rotary valves of instruments such as hematology instruments are periodically disassembled and cleaned by immersing the stators and rotor separately in cleaning solution and rinsing. Such a process is time consuming, manual and can interfere with the orderly processing of specimens. The necessity of periodic (e.g., daily or weekly) disassembly and assembly of the rotary shear valve also introduces the possibility of contamination or error.

BRIEF DESCRIPTION OF THE PRESENT INVENTION

The present invention relates to an improvement in such rotary shear valves, especially for hematology instruments, having provision made for cleaning the portions of the shear valve most likely to require periodic cleaning without disassembly of the shear valve. Such portions generally requiring cleaning include the specimen pathway, the one or more dispensing pathways formed in the second rotary position and (by use of a third rotary position) the portions of the rotor surfaces most likely to require cleaning.

Thus, the present invention provides, in one form, a rotary shear valve comprising a substantially disc-shaped front stator, a substantially disc-shaped rear stator and a rotor between and parallel to the front and rear stators, forming in a first rotary position a specimen pathway including a first normal passage through the rotor, and forming in a second rotary position a sample dispensing pathway including the first normal passage through the rotor, means for introducing specimen into the specimen pathway with the rotor in the first rotary position, and means for flushing fluid through the sample dispensing pathway when the rotor is in the second rotary position to withdraw an aliquot of specimen which is within the first normal passage;

characterized by circumferentially-extending concave arced grooves being formed in the rear face of the front stator and in the front face of the rear stator, and by the rotary shear valve further comprising means for introducing cleaning solution into the concave arced grooves with the rotor in a third rotary position, each concave arced groove communicating in the third rotary position with a circumferentially-extending portion of a face of the rotor adjacent to the first normal passage.

The present invention further comprises a method for operating a rotary shear valve of the type wherein specimen is introduced into the rotary shear value with the rotor in a first rotary position, an aliquot of specimen is dispensed from the rotary shear valve with the rotor in a second rotary position, the dispensing pathway is rinsed with the rotor in the second rotary position and the specimen pathway is rinsed with the rotor in the first rotary position;

characterized by periodically rotating the rotor to a third rotary position remote from the first and second rotary positions and introducing cleaning solution into circumferentially-extending concave arced grooves formed in the rear face of the front stator and in the front face of the rear stator in contact with portions of faces of the rotor at the radius of and adjacent to each passage through the rotor which forms a part of the specimen pathway in the first rotary position and also adjacent to and at the radius of each passage through the rotor which forms a portion of a dispensing pathway in the second rotary position.

DETAILED DESCRIPTION OF THE INVENTION

The present invention involves an improvement in a rotary shear valve having front and rear stators and a rotor sandwiched therebetween. The present invention can be illustrated by an embodiment of rotary shear valve illustrated in the FIGS., and as described below. After the discussion of such illustrative embodiment, various alternative embodiments and other features of the present invetion will be described.

Figure 1:
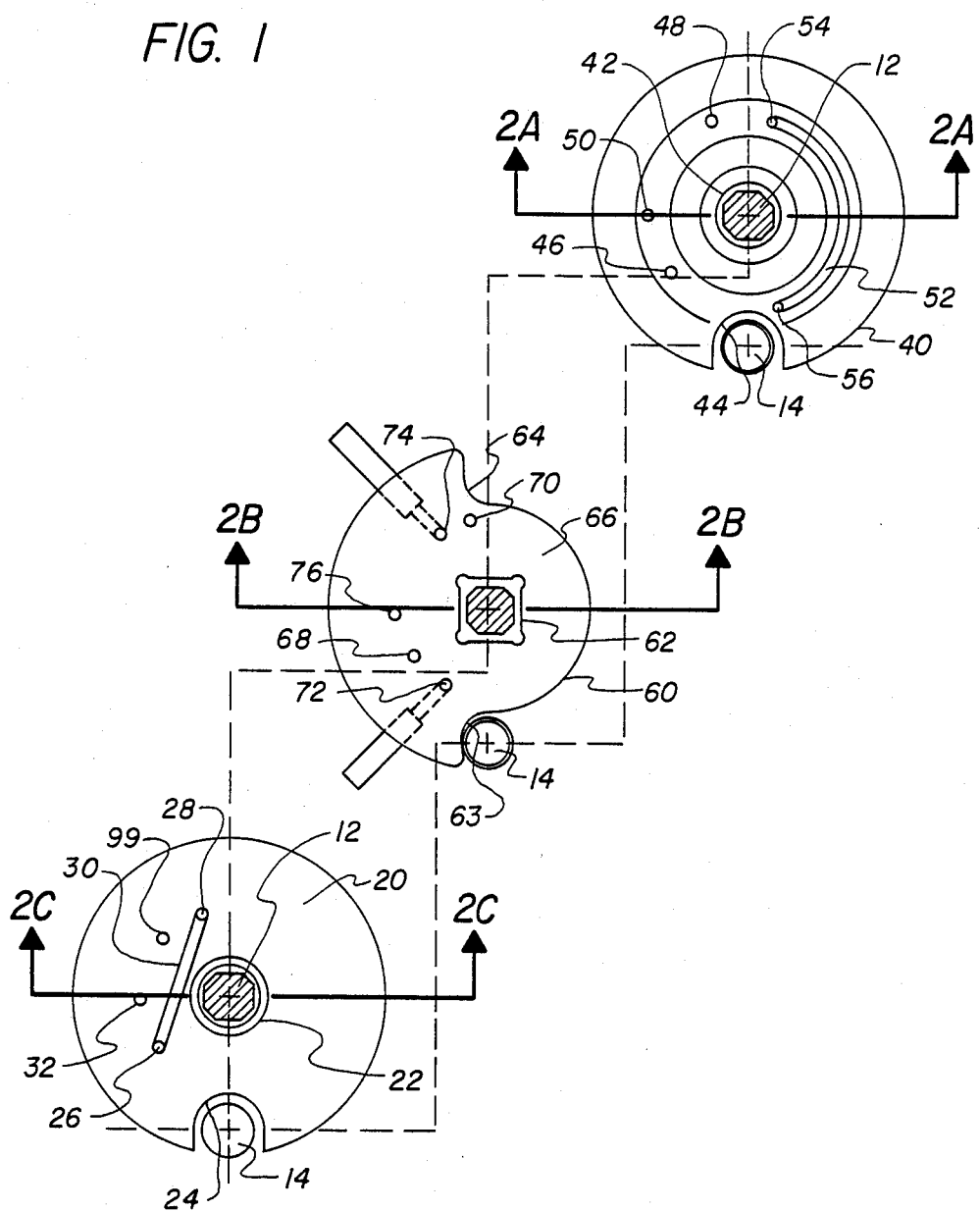

FIG. 1 is front view of the components of a shear valve assembly 10, representing an embodiment of the present invention in a first rotary position, sometimes referred to hereafter as the home position. Front stator 20, rotor 60 and rear stator 40 are parallel and (when assembled) are aligned around on axle 12 and a lower bar 14. Axle 12 and lower bar 14 each extend horizontally and normal to the vertical plane of the front stator 20, rotor 60 and rear stator 40.

Figure 2C:
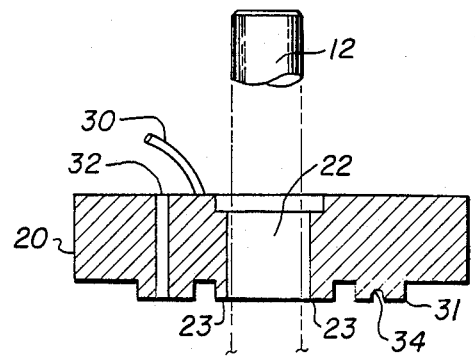

Front stator 20, as illustrated in FIG. 1 and in section in FIG. 2C, is generally disc-shaped. Center hole 22 through the front stator 20 contains axle 12 in the assembled shear valve. The lower recess 24 in front stator 20 contains in the assembled shear valve the bar 14. A WBC inlet passage 26 extends normally through the front stator 20 at a defined radius R and can be considered at 240° (8:00 clock position) in the home position. A WBC outlet passage 28 extends normally through front stator 20 at 345° (11:30 clock position). A looped tube 30 extends forward of the front stator 20 and connects the forward end of passage 26 to the forward end of passage 28. The WBC loop 30, the WBC inlet passage 26 and the WBC outlet passage 28 together define a WBC specimen chamber of 40 microliters in volume. An RBC dilution inlet passage 32 extends normally through the front stator at radius R at a position 30° clockwise from WBC inlet passage 26 and thus is indicated in FIG. 1 to be at 270° (9:00 clock position). An arced cleaning channel 34 is formed at radius R in the rear (inner) face of front stator 20 and extends from 30° (1:00 clock position) to 165° (5:30 clock position). A priming passage 99 extends normally through the front stator 20 at radius R and 315° (10:30 clock position).

The rear stator 40 is also generally disc-shaped. As with the front stator 20, rear stator 40 is provided with a center hole 42 (through which axle 12 extends in the assembled shear valve) and a lower recess 44 through which bar 14 extends in the assembled shear valve. A specimen inlet passage 46 extends normally through the rear stator 40 at 240° and at radius R. A specimen outlet passage 48 extends normally through the rear stator 40 at radius R and 345°. An RBC dilution exit passage 50 extends normally through rear stator 40 at radius R and 270°. An arced cleaning channel 52 is formed in the front (inner) face of the rear stator 40 at radius R and extends from 30° to 165°. A cleaning solution inlet passage 54 extends normally through rear stator 40 at radius R and 30° and thus communicates with one end of the arced cleaning channel 52. A cleaning solution outlet passage 56 extends normally through rear stator 40 at adius R and 165°, and thus communicates with the opposite end of the arced cleaning channel 52.

The rotor 60 is generally shaped in the form of a half disc except for the square center hole 62 with four small circular extended corners, lower and upper recesses 63 and 64 and inner ring portion 66 described below. The center hole 62 through rotor 60 is traversed and engaged for rotation by axle 12 in the assembled shear valve 10. A lower recess 63 at an exterior corner of the rotor 60 engages bar 14 in the first or home position. An upper recess 64 is formed in the upper exterior corner of the half disc of rotor 60 to engage bar 14 in the third or face-cleaning position described below. An inner ring portion 66 of the rotor forms a full circle around center hole 62, and thus represents the only significant portion of rotor 60 in excess of the half disc shape.

An RBC sample passage 68 extends normally through the rotor 60 at radius R and 240° in the home position and holds a volume of 1.6 microliters. A specimen outlet passage 70 extends through rotor 60 at a radius R and 345°. A WBC dilution passage 72 extends through the rotor 60 at 210° and has an inlet on the outer edge of the rotor 60, extends radially inward to radius R and then extends normally forward to an outlet on the front face of the rotor 60. A WBC diluted sample passage 74 at 315° has an inlet on the front face of rotor 60 at radius R, extends rewardly into the rotor 60 and then radially outward to an outlet on the outer edge of rotor 60, but still at 315°.

In the first (home) position, a specimen of blood is introduced into the specimen pathway formed by passage 46, RBC sample passage 68, WBC inlet passage 26, WBC loop 30, WBC outlet passage 28, specimen outlet passage 70 and specimen outlet passage 48. This pathway is sometimes referred to hereafter as the specimen pathway.

A diluent passage 76 is also provided at 270° through the rotor so that a straight-through diluent pathway (passages 50, 76 and 22) is formed in the first rotary position. This diluent pathway is filled with diluent while the specimen pathway is filled with specimen.

The rotor 60 is then rotated clockwise 30° so that the RBC sample passage 68 is now aligned with passages 32 and 50, and passages 72 and 74 are aligned, respectively, with passages 26 and 28. Each rotation of the rotor 60 is caused by rotating, axle 12; stators 20 and 40 are held stationery by bar 14. This second or dispensing position is indicated by Table II, below. Since the entire specimen pathway was filled with specimen (e.g., blood) it should be appreciated that upon rotation this specimen has been divided into five continuous proportions or aliquots, four small aliquots in passages 46, 48, 68 and 70 and one large aliquot in the continuous pathway portion formed by passages 26 and 28 and tube 30.

In the second rotary position diluent is now introduced through the front of RBC dilution inlet passage 32 to dilute the 1.6 microliter RBC sample (one of the four small aliquots of the specimen) in RBC sample passage 68. The diluted RBC sample is dispensed through the RBC dilution exit passage 50 and into the RBC channel of the instrument. To avoid air bubbles on either side of this sample aliquot, passages 32 and 50 had been filled with diluent. Thus passages 32, 68 and 50 define in the second rotary position a dispensing pathway into the RBC channel. In the RBC channel of the instrument, an impedance measurement is made of total cells, mean cell volume and other values of the RBC sample.

Simultaneously, in the second rotary position or dispensing position, diluent is introduced radially into the WBC dilution entrance 72 to dilute the 40 microliter WBC sample (another aliquot of the specimen) in passages 26 and 28 and loop 30. The diluted WBC sample is dispensed radially outward through WBC diluted passage 74 and into the WBC channel of the instrument. Passages 26, 28, 70 and 72 and loop 30 therefor form a second dispensing pathway through the rotary shear valve 10 in the second rotary position called hereafter the WBC dispensing pathway. In the WBC channel of the instrument, after being mixed with lysing reagent and more diluent, an impedence measurement is made of the white cells (those intact after lysing), as well as an optical measurement of the cyanohemoglobin formed by the reaction of cyanide in the lysing reagent with hemoglobin in the lysed red cells. Such lysing reagent may be conveniently flushed through the WBC pathway formed by elements 74, 28, 30, 26 and 72.

Still in the second position, diluent for producing the dilutions is dispensed and rinses the RBC pathway (elements 32, 68 and 50) and the WBC pathway (elements 72, 26, 30, 28 and 74) with diluent. Next, the rotor is rotated 30° counter-clockwise back to the first or home position, where the specimen pathway (elements 46, 68, 26, 30, 28, 70 and 48) is now rinsed with diluent to remove especially the unused aliquots of blood specimen which were left in passages 46, 70 and 48. The rinse is conveyed to waste by valving exterior to the rotary shear valve.

The positioning of the first and second rotary positions and third rotary position (described below) is summarized in the following tables.

TABLE I

First Rotary Position (Home)

| Angular Position | Stator 40 | Rotor 60 | Stator 20 | Loop 30 |
|---|---|---|---|---|
| 0° (12:00) | | 64 | | |
| 345° (11:30) | 48 | 70 | 28 | end |
| 315° (10:30) | | 74* | 99 | |
| 270° (9:00) | 50 | 76 | 32 | |
| 240° (8:00) | 46 | 68 | 26 | end |
| 210° (7:00) | | 72* | | |
| 180° (6:00) | 44 | 63 | 24 | |
| 165° (5:30) | 54 | | | |
| 30° (1:00) | 56 | | | |

*opening radially and to stator 20, but not to stator 40.

TABLE II

Second Rotary Position (Dispensing)

| | Stator 40 | Rotor 60 | Stator 20 | Loop 30 |
|---|---|---|---|---|
| 345° (11:30) | 48 | 74* | 28 | end |
| 315° (10:30) | | | 99 | |
| 300° (10:00) | | 76 | | |
| 270° (9:00) | 50 | 68 | 32 | |
| 240° (8:00) | 46 | 72* | 26 | end |
| 210° (7:00) | | 63 | | |
| 180° (6:00) | 44 | | 24 | |
| 165° (5:30) | 54 | | | |
| 30° (1:00) | 56 | 64 | | |

TABLE III

Third Rotary Position (Face - Cleaning)

| | Stator 40 | Rotor 60 | Stator 20 | Loop 30 |
|---|---|---|---|---|
| 0° (12:00) | | 63 | | |
| 345° (11:30) | 48 | | 28 | end |
| 315° (10:30) | | | 99 | |
| 270° (9:00) | 50 | | 32 | |
| 240° (8:00) | 46 | | 26 | end |
| 180° (6:00) | 44 | 64 | 24 | |
| 165° (5:30) | 54 | 70 | | |
| 135° (4:30) | | 74* | | |
| 90° (3:00) | | 76 | | |
| 60° (2:00) | | 68 | | |
| 30° (1:00) | 56 | 72* | | |

The several pathways through the rotary shear valve in the three positions are summarized by the following Table:

TABLE IV

PATHWAYS THROUGH ROTARY VALVE

| Rotary Position | Passages | Name |
|---|---|---|
| First | 48-70-28-30-26-68-46 | Specimen |
| First | 50-76-32 | Diluent Filling |
| First | 74-99 | WBC Priming |
| Second | 50-68-32 | RBC Dispensing |
| Second | 74-28-30-26-72 | WBC Dispensing |
| Third | 54-52-56 | Rear Cleaning |
| Third | 56-70-34-72 | Front Cleaning |

Such a pattern of filling, dispensing and rinsing steps in two rotary positions of the rotary shear valve is now conventional for using shear valve assemblies in hematology instruments. In the conventional instruments, however, it is necessary to periodically (e.g., daily or weekly, depending upon the intrument and its frequency of use) remove and disassemble the shear valve for cleaning. In such cleaning, the faces of the stators and rotor, the various passages through them and the WBC loop 30 are manually contacted or filled by cleaning solution, soaked and finally rinsed with diluent. Thereafter, the shear valve must be reassembled and reintroduced into the instrument before use (commonly after rinsing the pathways of the assembled rotary shear valve in the first and second rotary position)

In the method of the present invention and in the use of the rotary shear valve of the present invention, a cleaning cycle can be initiated either manually or automatically (e.g., upon instrument shut-down or once no samples have been introduced for a period of time after a predetermined degree of usage) with the shear valve assembly still intact and in the instrument. In the first two stages of the cleaning cycle, cleaning solution is introduced in the first (home) rotary position into the specimen passage formed by elements 46, 68, 26, 30, 28, 70 and 48. After soaking, the specimen pathways are rinsed with diluent. Next the rotor is rotated 30° into the second rotary position (the dispensing position) where cleaning solution is introduced into both the RBC dispensing pathway (elements 32, 68 and 50) and WBC dispensing pathway (elements 72, 26, 30, 48 and 74) and permitted to soak.

For the third and fourth stages of the cleaning cycle, the rotor is then rotated clockwise an additional 150°, until the bar 14 engages the upper recess 64 formed in the rotor 60, into a third or face-cleaning rotary position summarized in Table III, above. In the third stage of the cleaning cycle, the exterior port of passage 72 of the rotor is valved off. Cleaning solution is introduced through cleaning solution inlet 54, along arced cleaning channel 52 and out through cleaning solution outlet 56. By soaking in this position, the portion of the rear face of rotor 60 along the arced radius R from passage 70 (at 165°) to passage 72 (at 30°) is contacted by cleaning solution. This portion of the rear rotor is a major source of dried blood build-up, since any of the specimen (in the first postion) left between passage 46 and passage 68 will be smeared (by the 30° clockwise rotation of the rotor) along the rear face of the rotor between passage 68 and passage 72. Similarly, any of the specimen (in the first position) left between passage 70 and passage 48 will be smeared along the rear face of rotor 60 between passage 70 and passage 74. Furthermore, the only portion of the rear rotor face likely to be covered with dry blood is the arc from passage 70 to passage 72.

The fourth cleaning stage is also performed in the third (face-cleaning) postion. Passage 54 is now valved shut and the radially exterior end of passage 72 is now connected to the cleaning solution. Cleaning solution is now introduced into the pathway formed by elements 56, 70, 34 and 72 so that cleaning solution in arced channel 34 can contact the front face of the rotor from passage 70 to passage 72. It should be appreciated that this arced portion of the front face of rotor 60 contains the other two major points of dried blood build-up left (in the home position): between passages 68 and 26 (which was smeared along the front face from passage 68 to passage 72 when the rotor is rotated 30° to the dispensing position), and between passages 68 and 70 (which was smeared along the front face from passage 70 to passage 74 during the 30° rotation of the rotor). The passages are permitted to soak in the cleaning solution; then, the rotor returns to each of the three positions and the cleaning solution is rinsed away from each pathway. If the instrument is to return to operation, such rinse is with diluent; if the instrument is to be shut down, the rinse is with a rinse solution containing a preservative but no salt.

Optionally, the interior faces of the stator may also be cleaned and rinsed while the rotor is in the third position. It should be appreciated that both the rear face of front stator 20 and the front face of rear stator 40 in the vicinity of passages 26, 28 and 32 and of passages 46, 48, and 50 are, in the third position, communicating with the inner ring portion 66 of rotor 60 on the side of rotor 60 which is on the right in FIG. 1. A third and fourth channel could be formed in either side of rotor 60 at radius R and from 60° to 165° in the first rotary position (245° to 345° in the third rotary position). Then, by a variety of techniques, cleaning solution could be introduced into the third and fourth channels in the third rotary position to clean the portions of the front face of the rear rotor and the rear face of the front rotor likely to contain smeared specimen. The third and fourth channels would be rinsed of cleaning solution following the period of soaking.

The cleaning cycle completed, the rotor is then rotated counter-clockwise, either 180° back to the home position (for receipt of specimen) or, preferably 150° counter-clockwise to the second position for a rinse of the WBC and RBC dispensing pathways and then 30° further counter-clockwise back to the home position for a rinse of the specimen pathway before a new specimen is introduced.

Figure 2B:
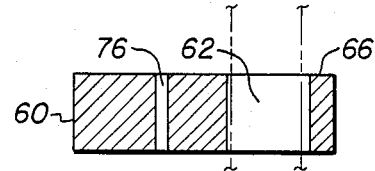
Figure 2A:
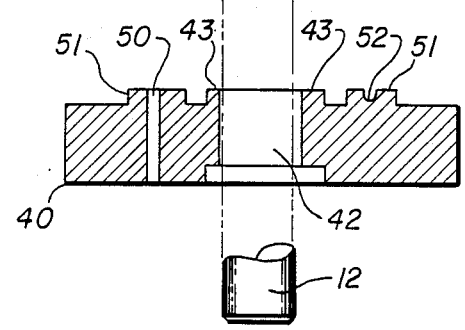

FIG. 2A illustrates a sectional view through the rear stator 40 at the 270°-(9:00)-90°(3:00) angular positions and through the center of center hole 42. The center hole 42 is counterbored on the rear side to receive the axle 12. On the front side of stator 42, a first raised annular portion 43 surrounds the center hole 42. A second raised annular portion 51 is also formed on the front face of rear rotor 40, extending both inwardly and outwardly from radius R. In the view shown in FIG. 2A, both the RBC exit passage 50 (a through hole) and arced groove 52 can be seen formed in raised portion 51.

FIG. 2B illustrates a similar sectional view of the rotor 60 in the first rotary position. Diluent passage 76 can be seen passing through the rotor 60 at 270° (9:00).

FIG. 2C illustrates a similar sectional view of the front stator 20. First raised annular portion 23 on the rear face of stator 20 surrounds center hole 22. Second raised annular portion 31 on the rear face of stator 20 extends both inwardly and outwardly from radius R. At 270° (9:00), the RBC dilution inlet extends through raised portion 31 and front stator 20. At 90° (3:00), arced groove 34 is formed in raised portion 31. WBC loop 30 can also be seen in cross-section at 270° (9:00).

In assembling the shear valve 10 in the first rotary position, the stators 20 and 40 and rotor 60 are aligned as shown in FIGS. 2A, 2B and 2C. An axle 12 and bar 14 are fitted through, respectively, center hole 42, 62 and 22 and recesses 44, 63 and 24.

In the assembled shear valve 10, both faces of the rotor 60 at radius R are engaged by raised portion 31 of stator 20 and raised portion 51 of stator 40. Annular portion 66 of rotor 60 is engaged by inner raised portions 23 and 42 of stators 20 and 40. A platinum strip can be provided on rotor 60 from recess 63 to recess 64. Suitable electrical connection of this strip to a control circuit and of the bar 14 to the control circuit can be used to determine when the rotor has reached the first or third rotary position. The shear valve assembly 10 is held together by a spring pressing a bushing around axle 12 forwardly against the rear of rear stator 40, so as to compress rear stator 40, rotor 60 and front stator 20 at the radial positions of raised portions 43 and 51 against a rotating bearing held in place by a thumbscrew around axle 12 forwardly of front stator 20.

Numerous variations are contemplated in the shear valve assembly 10 shown in the FIGS.. For example, the specimen pathway in the home position traverses the rotor twice and, upon rotation to the dispensing position, divides the specimen pathway into 5 aliquots, only two of which are dispensed into the instrument. Embodiments are contemplated in which the rotor is traversed only once or is traversed three or more times by the specimen pathway. Embodiments are also contemplated in which more or less of the aliquots of specimen are dispensed in the second rotary position (or in further rotary positions) into various channels of an instrument. The cleaning feature provided in the present invention, without requiring disassembly of the rotary shear valve, has obvious applicability to any such modification of the specimen pathway and dispensing steps, with suitable modification of various passages through the stator and rotor being made as required to achieve such variations. Those portions of the cleaning cycle which are performed in the first and second rotary positions could apply to whatever specimen pathways and dispensing pathways are used in those positions for the normal specimen introducing and diluted sample dispensing steps.

Upon rotation of the rotor to the third (face-cleaning) rotary position, it is important for the present invention that the circumferentially-extending concave arced grooves formed in the rear face of the front stator (such as arced cleaning channel 34) and in the front face of the rear stator (such as arced cleaning channel 52) be in contact with those portions of the rotor face likely to contain smeared sample. Thus, if the specimen pathway traverses the rotor only once in the first position, and any smear from that point of traverse extends only along one arced portion of the rotor face from the traversing passage to a point circumferentially spaced from that passage by the number of degrees of arc that the rotor is rotated to the various dispensing positions, then the arced grooves need only have a corresponding number of degrees of arc in order to communicate with any such smeared portions In addition to variations in the position and size the arced grooves, it should be apparent that a variety of arrangements are suitable for introducing cleaning solution into the arced grooves. In the FIGS., arced cleaning channel 34 is fed indirectly, but arced cleaning channel 52 is fed in the embodiment shown directly through the rear stator 40 via cleaning solution inlet 54 and cleaning solution outlet 56. It is contemplated, in some embodiments, to feed both arced cleaning channels directly through, respectively, the front stator 20 and the rear stator 40. It is also contemplated, in other embodiments, to feed both arced cleaning channels indirectly. Furthermore, while it is preferred to have a separate passage for the introduction of cleaning solution and withdrawal of cleaning solution, with proper venting, the two may occur through the same passage. Finally, it is preferred that cleaning solution be introduced into each arced cleaning channel adjacent to one of its ends and withdrawn from the arced cleaning channels adjacent to the opposite of its ends. Such an arrangement facilitates both rapid flow of cleaning solution through the arced channel prior to soaking, complete filling of the arced cleaning channel with cleaning solution for soaking and complete rinsing of cleaning solution from the arced cleaning channel by diluent after soaking.

By indicating that frequent disassembly of the rotary shear valve can be avoided by the periodic cleaning steps made possible by the present invention, it should not be assumed that no disassembly for cleaning is ever required. For example, if no provision is made by a particular embodiment of the rotary shear valve for cleaning the interior surfaces of the stators, then disassembly and cleaning on some bases may be required to avoid an undesired degree of build up on those surfaces. It is believed, however, that the frequency of disassembly for cleaning is greatly reduced for the corresponding instrument and the corresponding number of samples run through the instrument by providing for the cleaning cycle of the present invention. Thus, for example, in an instrument which, under normal use conditions, would require disassembly for cleaning on a weekly basis using a conventional rotary shear valve, such disassembly for cleaning may be conducted only monthly or bimonthly by using a rotary shear valve according to the present invention.

What is claimed is:

1. A rotary shear valve comprising a substantially disc-shaped front stator, a substantially disc-shaped rear stator and a rotor between and parallel to the front and rear stators, forming in a first rotary position a specimen pathway including a first normal passage through the rotor, and forming in a second rotary position a sample dispensing pathway including the first normal passage through the rotor, means for introducing specimens into the specimen pathway with the rotor in the first rotary position, and means for flushing fluid through the sample dispensing pathway when the rotor is in the second rotary position to withdraw an aliquot of specimen which is within the first normal passage;

wherein the rotary shear valve further comprises a first circumferentially-extending concave arced groove formed in the rear face of the front stator and a second circumferentially-extending concave arced groove formed in the front face of the rear stator, and the rotary shear valve further comprising means for introducing cleaning solution into the first and second circumferentially-extending concave arced grooves with the rotor in a third rotary position.

each circumferentially-extending concave arced groove communicating in the third rotary position with a circumferentially-extending portion of a face of the rotor adjacent to the first normal passage, and each circumferentially-extending concave arced groove being distal from the first normal passage in the first and second rotary positions.

2. The rotary shear valve of claim 1 wherein the specimen pathway further includes a second normal pathway through the rotor and wherein the circumferentially-extending concave arced grooves each communicate in the third rotary position with a portion of a face of the rotor adjacent to the first and second normal passages.

3. The rotary shear valve of claim 2 wherein the means for introducing cleaning solution comprises passages normally through the front stator into the first circumferentially-extending arced groove formed on the rear face of the front stator.

4. The rotary shear valve of claim 2 wherein the means for introducing cleaning solution comprises passages extending normally through the rear stator into the circumferentially-extending arced groove formed in the second front face of the rear stator.

5. The rotary shear valve of claim 2 wherein the means for introducing cleaning solution comprises a passage formed in the rotor which, in the second rotary position, forms a portion of a sample dispensing pathway.

6. The rotary shear valve of claim 1 wherein the means for introducing cleaning solution comprises passages extending normally through the front stator into the first circumferentially extending arced groove formed in the rear face of the front stator.

7. The rotary shear valve of claim 1 wherein the means for introducing cleaning solution comprises passages extending normally through the rear stator into the second circumferentially-extending arced groove formed in the front face of the rear stator.

8. The rotary shear valve of claim 1 further comprising means for introducing cleaning solution into the specimen pathway when the rotor is in the first rotary position and means for introducing cleaning solution into the sample dispensing pathway when the rotor is in the second rotary position.

9. The rotary shear valve of claim 1 wherein the rear face of the front stator and the front face of the rear stator each comprise circumferentially extending raised annular portion having a flat portion in contact with the rotor, which flat portion is wider in a radial direction than the first normal passage and which contacts the rotor at the radial position of the first normal passage, and wherein each circmferentially-extending concave arced groove is formed in a flat portion of a circumferentially extending raised annular portion.

* * * * *